(12) United States Patent
Rozzoni et al.

(10) Patent No.: US 11,807,600 B2
(45) Date of Patent: Nov. 7, 2023

(54) SYNTHESIS OF NOVEL KETONE BODY ANALOGS FOR USE AS A NUTRITIONAL SUPPLEMENT

(71) Applicants: Samuel J. Rozzoni, Racine, WI (US); Daryl R. Sauer, Trevor, WI (US)

(72) Inventors: Samuel J. Rozzoni, Racine, WI (US); Daryl R. Sauer, Trevor, WI (US)

( * ) Notice: Subject to any disclaimer, the term of this patent is extended or adjusted under 35 U.S.C. 154(b) by 141 days.

(21) Appl. No.: 17/525,663

(22) Filed: Nov. 12, 2021

(65) Prior Publication Data

US 2023/0150913 A1   May 18, 2023

(51) Int. Cl.
*C07C 69/18* (2006.01)
*A23L 33/10* (2016.01)
*C07C 69/21* (2006.01)

(52) U.S. Cl.
CPC .............. *C07C 69/18* (2013.01); *A23L 33/10* (2016.08); *C07C 69/21* (2013.01)

(58) Field of Classification Search
CPC .................................. C07C 69/14; C07C 69/16
See application file for complete search history.

(56) References Cited

U.S. PATENT DOCUMENTS

| | | | |
|---|---|---|---|
| 5,349,026 A * | 9/1994 | Emmons | C09D 157/00 525/379 |
| 8,101,653 B2 | 1/2012 | Veech | |
| 8,642,654 B2 | 2/2014 | Clarke | |
| 10,245,243 B1 | 4/2019 | Millet | |
| 2004/0176449 A1 | 9/2004 | Abraham | |
| 2012/0064611 A1 | 3/2012 | Robertson | |
| 2013/0102663 A1 | 4/2013 | Clarke | |
| 2015/0164855 A1 | 6/2015 | Clarke et al. | |
| 2016/0184248 A1 | 6/2016 | Hoffman | |
| 2018/0055797 A1 | 3/2018 | Llosa et al. | |
| 2018/0057846 A1 | 3/2018 | Llosa et al. | |
| 2019/0119705 A1 | 4/2019 | Llosa et al. | |
| 2019/0321309 A1 | 10/2019 | Millet | |

FOREIGN PATENT DOCUMENTS

WO   WO-2023283654 A1 *  1/2023
WO   WO-2023054702 A1 *  4/2023

OTHER PUBLICATIONS

Birkhahn, R.H.; Synthesis and Intravenous Infusion into the rat of Glyceryl Bisacetoacetate; Journal; 1997: 155-172; 78 (1); British Journal of Nutrition; Great Britain.
Clemens R.J.; Acetoacetylation with 2,2,6-Trimethyl-4H-1,3-dioxin-4-one: A Convenient Alternative to Diketene; Journal; 1985; 2431-2435; 50; J. Org. Chem (ACS), U.S.
Desrochers, S.; H. Metabolism of R- and S-1,3-Butanediol in Perfused Livers from Meal-Fed and Starved Rates; Journal 1992; 285; 647-653; Biochem. J.; Great Britain.
Clarke, K.; Kinetics, safety and tolerability of (R)-3-hydroxybutyl (R)-3-hydroybutyrate.; Journal; 2012; 63; 401-408; Regulatory Toxicology and Pharmacology; Netherlands.
Laplante, M.; mTOR signaling at a glance; Journal; Journal of Cell Science; 2009; 122; 3589-3594; The Company of Biologists; United Kingdom.
Pimentel, G. D.; b-Hydroxy-b-methylbutyrate (HMB) supplementation stimulates skeletal muscle hypertrophy; Journal; Feb. 23, 2011; 8(1);11; Nutrition & Metabolism; London, GB.
Desrochers, S.; R,S-1,3-butanediol acetoacetate esters, potential.;Journal; 1995; 6; 111-118; Nutritional Biochemistry; Elsevier Science Inc; New York, U.S.
Vittal, S.; The Populatio Pharmacokinetics of D-β-hydroxybutyrate Following Administration; The AAPS Journal; 2016; 678-688; vol. 18 No. 3.; U.S.
Cheong, Ling-Zhi; Chemo-enzymatic Synthesis of Novel-b-Hydroxy-b-methylbutyric Acid (HMB); Journal Am Oil Chem Soc; 2013; 919-922; 90; Springer; U.S.
Ortiz, C.; Novozym 435: the "perfect" lipase immobilized biocatalyst?; Journal, Catal. Sci. Technol; 2019; 2380-2420; 9 (10); The Royal Society of Chemistry; London, U.K.
Belsito, D. V et al (Scientific Analyst, S.; Heldreth B. Safety Assessment of Alkane Diols as Used in Cosmetics, 2014).
Dews, B. Caffeine. Annu Rev Nutr. 1982, 2, 323-341 Laboratory of Psychobiology, Department of Psychiatry, Harvard Medical School, Boston, Massachusetts, 02115.

* cited by examiner

*Primary Examiner* — Changqing Li
(74) *Attorney, Agent, or Firm* — VITALE, VICKREY, NIRO, SOLON & GASEY LLP

(57) ABSTRACT

When a healthy and balanced diet is not achieved, nutritional supplements are used to help deal with the resulting health issues and enhance the body's performance. The present invention relates to a novel category of molecules that combine the properties of both ketone bodies and β-Hydroxy β-Methylbutyrate (HMB) that can be used as supplements for treating a wide range of health-related issues. Acetoacetate and β-Hydroxybutrate along with isopentyldiol were used as the sources of ketone bodies and HMB, respectively. The present invention provides a method of synthesis for a new group of compounds that incorporate the properties found in acetoacetate and 3-hydroxybutyrate molecules with that of β-hydroxy β-methylbutyrate.

20 Claims, No Drawings

SYNTHESIS OF NOVEL KETONE BODY ANALOGS FOR USE AS A NUTRITIONAL SUPPLEMENT

FIELD OF THE INVENTION

The present invention relates to the synthesis of novel compounds, more specifically ketone body analogs for use as nutritional supplements.

BACKGROUND OF THE INVENTION

Ketone bodies are metabolites that the human body forms through the breakdown of fats during times of low food intake or other health related issues. Three major ketone bodies are acetoacetate, β-hydroxybutyrate, and acetone. Acetoacetate and β-hydroxybutyrate will be further metabolized to generate energy for the body, with acetone being a by-product Ketone bodies can be externally supplemented to achieve benefits without the breakdown of fats. Besides the use of ketone bodies as an energy source there are more health benefits, such as helping with weight loss, aging, diabetes, Alzheimer's, Parkinson's, seizures, cancer, psychiatric disorders, and issues dealing with irregular glucose metabolism. Ketone body esters, which are metabolically bioavailable versions of ketone bodies, have been shown in supplement form to encompass the beneficial aspects of ketone bodies.

β-Hydroxy β-methylbutyrate is a molecule that is available from natural sources such as catfish, aged meats, grapefruit and corn, however, it is available only in small quantities. β-Hydroxy β-methylbutyrate is obtained through the catabolism of the amino acid leucine, but with a low yielding conversion rate. The use of β-hydroxy β-methylbutyrate as a supplement has shown to have health benefits including activation of the mTOR kinase, which initiates protein synthesis to help build and repair muscles. The supplementation of β-hydroxy β-methylbutyrate has also been shown to prevent protein degradation. Preventing muscle loss and promoting the repair and development of muscles is important, especially in a variety of the population including athletes and the aging.

As a result of poor dietary habits and an increasing aging population, there is an expanding market for nutritional supplements. There are a wide variety of supplements on the market used to reduce the effects of insufficient nutrient intake, due to an array of health conditions. Many health conditions are related to lowered food intake, which reduces both physical and cognitive performance. Ketone bodies and β-hydroxy β-methylbutyrate, separately have been used as supplements to address the reduced physical and cognitive performance. The combination of these molecules into a single supplemental compound could potentially lead to synergistic effects. A look into the background of the ketone bodies and β-hydroxy β-methylbutyrate are needed to understand their capabilities as supplements.

Both ketone bodies and β-hydroxy β-methylbutyrate are significant compounds that can help a vast number of individuals, suffering from reduced physical or cognitive performances. There is a need for supplements that can combine the effects of both ketone bodies and β-hydroxy β-methylbutyrate. In summary, based on the above there is a need for new and novel molecules which would incorporate the benefits of both ketone bodies and β-hydroxy β-methylbutyrate.

SUMMARY OF THE INVENTION

The present invention provides the description of and a method to synthesize a novel and unique group of compounds that incorporate the beneficial properties found in ketone bodies such as acetoacetate and β-hydroxybutyrate in addition to the benefits seen with the supplementation of β-hydroxy β-methylbutyrate.

The present invention provides a method of synthesis for a new group of compounds that incorporate the properties found in acetoacetate and β-hydroxybutyrate molecules with that of β-hydroxy β-methylbutyrate.

In this present embodiment, a novel group of molecules which combine the structures of acetoacetate and or β-hydroxybutyrate bonded to 3-methyl-1,3-butanediol, a proposed metabolic precursor to β-hydroxy β-methylbutyrate are disclosed. This embodiment will allow for a novel and improved source of ketone bodies and β-hydroxy β-methylbutyrate as an administration in a single supplement.

Another aspect of the present invention relates to a reaction termed "transesterification." The synthesis of the molecules of the present invention utilizes a reaction called transesterification. Transesterification is a chemical exchange of R-groups between an ester and an alcohol to form new esters and alcohols with the ester typically being the desired product as shown in the equation below:

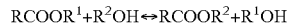

$$RCOOR^1 + R^2OH \leftrightarrow RCOOR^2 + R^1OH$$

The desired ester can also be prepared via an esterification reaction, where a carboxylic acid is reacted with an alcohol to form the new ester with water as a by-product:

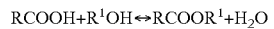

$$RCOOH + R^1OH \leftrightarrow RCOOR^1 + H_2O$$

In its principal embodiment, the present invention provides a compound of formula (I)

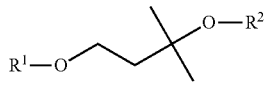

$R^1$ is selected from the group comprising of:
(a) Hydrogen, wherein $R^2$ is not hydrogen,
(b) Acetoacetyl ($CH_3COCH_2CO-$),
(c) β-Hydroxybutyryl ($CH_3CH(OH)CH_2CO-$),
(d) (R)-β-Hydroxybutyryl ($CH_3CH(OH)CH_2CO-$),
(e) (S)-β-Hydroxybutyryl ($CH_3CH(OH)CH_2CO-$);
$R^2$ is selected from the group comprising of:
(a) Hydrogen, wherein $R^1$ is not hydrogen,
(b) Acetoacetyl ($CH_3COCH_2CO-$),
(c) β-Hydroxybutyryl ($CH_3CH(OH)CH_2CO-$),
(d) (R)—β-Hydroxybutyryl ($CH_3CH(OH)CH_2CO-$),
(e) (S)-β-Hydroxybutyryl ($CH_3CH(OH)CH_2CO-$);
or a therapeutically acceptable salt, ester, or polymer thereof.

Asymmetric centers exist in the compounds of the present invention and are designated by the letters "R" or "S," depending on the configuration of substituents around the chiral carbon atom. It should be understood that the invention encompasses all stereochemical isomeric forms, both enantiomerically pure and any mixture thereof.

The compounds of formula (I) can be prepared via transesterification, esterification utilizing both enzymatic and nonenzymatic methods including microwave irradiation, sonication, photochemically, acid and base catalysis, soluble and supported enzymatic catalysis as well as other methods known to those skilled in the art.

In another embodiment the present invention provides a route of synthesis for compounds of formula (I) using but not limited to using enzymatic methods including a lipase.

Examples of immobilized enzymatic catalysts includes a vast number of lipases, but some of the most useful include the Porcine pancreatic lipase, lipase from *Candida rugosa*, and lipases from *Candida antarctica*.

In another embodiment the present invention provides a route of synthesis for compounds of formula (I) using acidic catalysts such as but not limited to hydrochloric, phosphoric, sulfuric, sulfonic acids and basic catalysts such as but not limited to metal alkoxides, oxides, acetates, and amines, for example 4-dimethylaminopyridine and triethylamine.

DEFINITIONS

The following explanations of terms and methods are provided to better describe the present disclosure and to guide those of ordinary skill in the art in the practice of the present disclosure.

"Acetoacetyl" refers to the functionality with the formula $CH_3COCH_2CO—$

"β-Hydroxybutyryl" refers to the functionality with the formula $CH_3CH(OH)CH_2CO—$ "Esterification" refers to the reaction of an alcohol with a carboxylic acid or a carboxylic acid derivative to give an ester.

"Transesterification" refers to the chemical exchange of functionalities between an ester and an alcohol to form new esters and alcohols.

The term "ester" is represented by the formula $—OC(O)R$, where R can be any organic group, typically an alkyl group.

"Derivative" refers to a compound or portion of a compound that is derived from or is theoretically derivable from a parent compound.

The term "hydroxy" is represented by the formula $—OH$.

The term "oxo," as used herein, represents $=O$.

"Polymer" is a molecule that has repeating units called monomers, as used herein represents repeating units of acetoacetyl or β-Hydroxybutyryl functionalities.

"Therapeutically acceptable" refers to those compounds (or salts, zwitterionic forms, esters, polymers, etc.) which are suitable for the treatment of diseases without undue toxicity, irritation, and allergic response, are commensurate with a reasonable benefit/risk ratio, and which are effective for their intended use.

While the above definitions are used in this application to describe how one of ordinary skill in the art may generally understand the terms used to describe the invention, the definitions are not intended to limit the definition of the above terms in any manner. It is understood that the terms have much broader meaning than set forth above to those of skill in the art. The terms as used to describe the present invention are simply meant to provide a general understanding of when the terms may be used.

DETAILED DESCRIPTION OF THE INVENTION

Elements of the present invention may be better understood from the following description of the preferred embodiments. The preferred embodiments are intended to provide a description of the present invention and are not intended to limit the invention in any manner.

The present invention relates to a category of a transesterification reaction. The category of transesterification reactions can be divided into subtypes based on the compounds used within the transesterification. One of those subtyped reactions is called a transacetoacetylation and it is defined as a transesterification of a nucleophile with an acetoacetate group to form a new acetoacetate ester:

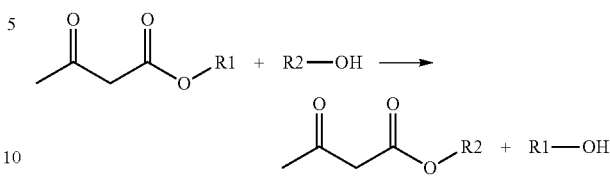

Acetoacetate esters have several applications in industries including agrichemical and polymer industries, but their importance for the synthesis of ketoesters will be discussed.

Compounds of the present invention comprise of the ketone bodies acetoacetate and β-hydroxybutyrate being bonded to a 3-methyl-1,3-butanediol molecule of the formula (I). Representative list of compounds in this invention of formula (I):

3-hydroxy-3-methylbutyl 3-oxobutanoate
3-hydroxy-3-methylbutyl 3-hydroxybutanoate
4-hydroxy-2-methylbutan-2-yl 3-oxobutanoate
4-hydroxy-2-methylbutan-2-yl 3-hydroxybutanoate
2-methyl-4-[(3-oxobutanoyl)oxy]butan-2-yl 3-oxobutanoate
4-[(3-hydroxybutanoyl)oxy]-2-methylbutan-2-yl 3-oxobutanoate
3-[(3-hydroxybutanoyl)oxy]-3-methylbutyl 3-oxobutanoate
4-[(3-hydroxybutanoyl)oxy]-2-methylbutan-2-yl 3-hydroxybutanoate Asymmetric centers exist in the compounds of the present invention and are designated by the letters "R" or "S," depending on the configuration of substituents around the chiral carbon atom. It should be understood that the invention encompasses all stereochemical isomeric forms, both enantiomerically pure and any mixture thereof. The invention also includes all therapeutically acceptable salts, esters, or polymers thereof.

The present invention generates new molecules that would contain the properties of both ketone bodies and β-hydroxy β-methylbutyrate. These molecules may be prepared using transesterification methods by both enzymatic and nonenzymatic procedures. The source of β-hydroxy β-methylbutyrate must be addressed in the present invention. To combine ketone bodies with β-hydroxy β-methylbutyrate, a different starting molecule would be necessary as a source of β-hydroxy β-methylbutyrate.

The production of compounds of formula(I) that contain an acetoacetyl $(CHL_3COCH_2CO—)$functionality are formed in both enzymatic and nonenzymatic routes of synthesis. 3-methyl-1,3-butanediol, also known as isopentyldiol, can be treated with a source of an acetoacetyl molecule such as, but not limited to, the acid or esters of acetoacetate including methyl acetoacetate, ethyl acetoacetate, tert-butyl acetoacetate, diketene, or 2,2,6-trimethyl-4H-1,3-dioxin-4-one. There does not currently exist a molecule that contains both the functionality of the group of the acid or esters of acetoacetate described above with the base formulation of formula (I). The reaction can be performed solventless or in various solvents, but not limited to ethyl acetate, toluene, xylene, or acetonitrile. The reaction is typically performed above room temperature and up to 150° C. While the preferred temperature for the reaction may be in the range of 20° C. to 150° C., it should be understood that reaction may take place above 150° C. and would likely provide for a faster reaction and reduce the byproducts of the reaction. However, this may occur at both lower and higher temperatures. The reactions may also be catalyzed with acids or bases such as sulfuric acid or triethylamine but are not limited to these compounds. The reaction can also be conducted with an enzyme, more specifically with a lipase in either the free form or immobilized on a solid support. The purification of these reactions to isolate the desired products may include column chromatography, distillation, extraction, and other more complex purification methods.

The production of compounds of formula (I) that contain a β-hydroxybutyryl ($CH_3CH(OH)CH_2CO-$) functionality can be formed from compounds with an acetoacetyl moiety utilizing a variety of reduction methods. The reduction can be performed using (but not limited to using) sodium borohydride or similar reducing agents in a protic solvent such as methanol and performing a reduction using a hydrogenating device including a Parr Shaker or a flow hydrogenator. There exist other methods that the reduction may be performed. For example, the reduction can also be achieved via enzymatic methods using but not limited to reductases or alcohol dehydrogenases. These methods should consider the R/S enantiomers that would be generated. As each method may generate a specific enantiomer, the selection of reaction parameters including catalysts should be taken with care. This invention encompasses both racemic mixes and enantiomerically pure products.

The compounds of formula (I) that contain a β-Hydroxybutyryl functionality can also be formed by reacting 3-methyl-1,3-butanediol, also known as isopentyldiol, with a source of the β-hydroxybutyryl functionality. The source of β-Hydoxybutyryl may be selected from the group β-hydroxybutyrate acid, esters of β-hydroxybutyrate such as ethyl-3-hydroxybutyrate, or β-Butyrolactone. There are other β-hydroxybutyrates that may satisfy the requirements of the compounds to create formula (I). The starting reagents should be enantiomerically pure if the desired product is one of the enantiomers, if not a mix of enantiomers will be formed. A portion of 3-methyl-1,3-butanediol can be treated with the β-Hydroxybutyryl source under a variety of parameters as describe for the synthesis of the desired reduced compound.

If the desired compound of formula (I) is to have only an acetoacetyl or β-Hydroxybutyryl functionality on the tertiary alcohol of 3-methyl-1,3-butanediol a synthesis containing protecting groups is required. A protecting group such as but not limited to silyl ethers or acetyl groups can be used to protect the primary alcohol to allow for chemoselectivity of only the tertiary alcohol. After the ketone body functionality has been attached to the tertiary alcohol, the protecting group can be removed by a sufficient deprotection step typically using an acid or base.

The present invention will now be described in connection with certain preferred embodiments which are not intended to limit its scope. On the contrary, the present invention covers all alternatives, modifications, and equivalents as can be included within the scope of the claims. The following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Example 1

The first example formula is 3-hydroxy-3-methylbutyl 3-oxobutanoate:

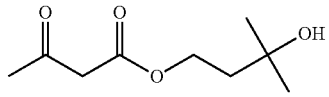

There are various methods to synthesis 3-hydroxy-3-methylbutyl 3-oxobutanoate. As explained below, one method of the synthesis of 3-hydroxy-3-methylbutyl 3-oxobutanoate involves 3-methyl-1,3-butanediol (2.02 g, 19.44 mmol) and mixing it with ethyl acetoacetate (1.87 g, 14.34 mmol) and Novozym 435 resin beads (0.19 g, 10% w/w acyl donor). The mixture may be stirred at 65° C. in a sand bath for 24 hours with a glass capillary pierced through a septum for removal of the ethanol by-product while the preferred method is to stir the mixture at 65° C. in a sand bath for 24 hours, those of ordinary skill in the art would understand that the mixture could be stirred using other methods at a variety of temperatures. Periodic TLC testing showed the consumption of the ethyl acetoacetate after 24 hours with unreacted 3-methyl-1,3-butanediol. To the mixture diethyl ether (5 mL) may be added to dissolve the mixture and then ran through a filter to separate off the beads. In a preferred method of filtering utilities, a plug of glass wool, but any known filtering system to separate the beads maybe used. The reaction mixture can be concentrated under vacuum. The crude oil can then be dissolved in acetonitrile (5 mL) and 4 equivalents of propanal (4.51 g, 77.58 mmol) proportional to the original quantity of 3-methyl-1,3-butanediol were added. The mix is placed in an ice bath and stirred while adding Amberlyst® 15 hydrogen form dry (0.45 g. 10% w/w propanal) before capping for 30 minutes. The reaction should be monitored by TLC to determine when all the 3-methyl-1,3-butanediol is consumed. Once consumed, the reaction was concentrated down under vacuum to resulting in the desired compound as an oil. MS m/c 173 [M—CH3]; $^1$H NMR ($CDCl_3$): δ 12.03 (s, 1H), δ 4.98 (s, 2H), β 4.49 (t, 2H), δ 3.47 (s, 2H), δ 2.27 (s, 3H), δ 1.96 (s, 3H), δ 1.78 (t, 2H), δ 1.27 (s, 6H); IR (neat) 3423, 2972, 2935, 1735, 1708, 1147 $cm^{-1}$.

Example 2

The second example formula is set forth for 3-hydroxy-3-methylbutyl 3-oxobutanoate:

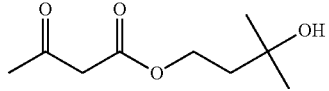

There are various methods to synthesis 3-hydroxy-3-methylbutyl 3-oxobutanoate. An explanation of how the formula was derived is described below. First 3-methyl-1,3-butanediol (1.01 g, 9.70 mmol) is mixed with methyl acetoacetate (1.61 g, 13.87 mmol) and Novozym 435 resin beads (0.14 g, 8.4% w/w acyl donor). The mixture can be stirred at 60° C. for 24 hours. While the preferred method calls for stirring the mixture at 60° C. for 24 hours, other methods of stirring may be utilized. The reaction mixture may be concentrated under vacuum. The crude oil may then be purified on silica gel with Heptane: EtOAc 1:1 resulting in the desired compound as an oil. MS; ¹H NMR; IR: See Example 1.

Example 3

The third example formula is set forth below for 3-hydroxy-3-methylbutyl 3-oxobutanoate:

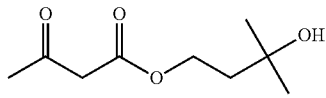

There are various methods to synthesis 3-hydroxy-3-methylbutyl 3-oxobutanoate. An explanation of how the formula was derived is described as follows. First, 3-methyl-1,3-butanediol (0.98 g, 9.41 mmol) is mixed with methyl acetoacetate (1.63 g, 14.04 mmol) and a catalytic amount of triethylamine (40 µL) was added. The reaction was heated at 100° C. for 24 hours. While the preferred method calls for heating the reaction to 100° C., it should be understood that higher temperatures may be utilized without departing from the nature of the invention. The reaction mixture can then be concentrated under vacuum. The crude oil is then purified on silica gel with Heptane: EtOAc 1:1 resulting in the desired compound as an oil. MS; ¹H NMR; IR: See Example 1.

Example 4

The fourth example formula is set forth below for 3-hydroxy-3-methylbutyl 3-oxobutanoate:

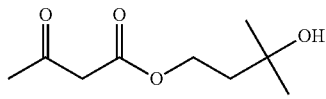

There are various methods to synthesis 3-hydroxy-3-methylbutyl 3-oxobutanoate. An explanation of how the formula was derived is described as follows. First, 3-methyl-1,3-butanediol (0.49 g, 4.74 mmol) was mixed with tert-butyl acetoacetate (1.01 g, 6.38 mmol) were vigorously stirred at 100° C. for 12 hours. The resulting mixture was concentrated under vacuum. The crude oil was then dissolved in acetonitrile (5 mL) and 4 equivalents of propanal (0.82 g, 14.11 mmol) to starting 3-methyl-1,3-butanediol were added. The mix was placed in an ice bath and stirred while adding Amberlyst® 15 hydrogen form dry (0.08 g, 10% w/w propanal) before capping for 30 minutes. The reaction was monitored by TLC to determine when all the 3-methyl-1,3-butanediol was consumed. Once consumed, the reaction was concentrated down under vacuum to resulting in the desired compound as an oil. MS; ¹H NMR; IR: See Example 1.

Example 5

The fifth example formula is set forth below for 3-hydroxy-3-methylbutyl 3-hydroxybutanoate:

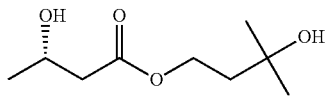

There are various methods to synthesis 3-hydroxy-3-methylbutyl 3-hydroxybutanoate. An explanation of how the formula was derived is described as follows. First, 3-methyl-1,3-butanediol (1.00 g, 9.64 mmol) was mixed with ethyl-3-hydroxybutyrate (0.63 g, 4.78 mmol), and Novozym 435 resin beads (0.06 g, 10% w/w acyl donor). The mixture was stirred vigorously in a 55° C. sand bath for 12 hours. While the preferred stirring method was set out above, it should be understood that other vigorous stirring methods at various temperatures without departing from the nature of the invention. The product was purified by preparative TLC. MS m/e 175 [M-CH3]; ¹H NMR: δ 4.32 (t, 2H), δ 2.53 (q, 1H), δ 2.39 (d, 2H), δ 1.86 (t, 2H), δ 1.28 (s, 6H), δ 1.17 (d, 3H); IR: 3385, 2970, 2929, 1714, 1170, 1070 cm⁻¹.

Example 6

The sixth example formula is set forth below for 3-hydroxy-3-methylbutyl 3-hydroxybutanoate:

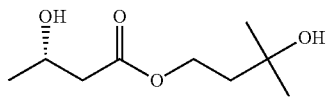

There are various methods to synthesis 3-hydroxy-3-methylbutyl 3-hydroxybutanoate. An explanation of how the formula was derived is described as follows. First, 3-methyl-1,3-butanediol (3.03 g, 29.11 mmol), ethyl acetoacetate (4.12 g, 31.67 mmol) and Novozym 435 (0.35 g, 8.5% w/w acyl donor) were mixed together. The mixture may be placed into an 80° C. sand bath and stirred vigorously overnight. While the preferred method calls for heating the reaction to 100° C., it should be understood that higher temperatures may be utilized without departing from the nature of the invention. After 18 hours the mixture was removed from the heat and the mixture was diluted with diethyl ether (10 mL) and filtered through a glass wool plug to remove the beads. Then a portion of the reaction mixture (1.00 g, 5.32 mmol) and sodium borohydride (0.16 g, 4.34 mmol) was dissolved in isopropanol (6 mL). The mixture is placed in an ice bath and stirred for 12 hours and allowed to reach room temperature. The mixture may be concentrated under vacuum and then diluted with dichloromethane (20 mL). The mixture may be washed two times with brine (10 mL) and then the organic layer is separated and dried with MgSO₄. The organic layer can be concentrated under vacuum resulting in a crude oil of the desired compound, which was further purified by preparative TLC. MS; ¹H NMR; IR: See Example 5.

Example 7

The seventh example formula is set forth below for 2-methyl-4-[(3-oxobutanoyl)oxy]butan-2-yl 3-oxobutanoate:

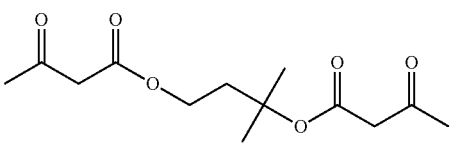 [SMILES: CC(=O)CC(=O)OCCC(C)(C)OC(=O)CC(C)=O]

There are various methods to synthesis 2-methyl-4-[(3-oxobutanoyl)oxy]butan-2-yl 3-oxobutanoate. An explanation of how the formula was derived is described as follows. First, to a solution of 3-methyl-1,3-butanediol (0.53 g, 5.09 mmol) and toluene (5 mL) was added 2,2,6-trimethyl-4H-1,3-dioxin-one (1.56 g, 10.94 mmol). The mixture may be stirred vigorously for 30 minutes in a 140° C. sand bath. While the preferred method calls for heating the reaction to 100° C., it should be understood that higher temperatures may be utilized without departing from the nature of the invention. Then to the mixture can be added diethyl ether (5 mL) and the mixture was filtered to remove the resin beads. The solution was concentrated under vacuum. The crude mix was analyzed to confirm the purity and identity of the desired product. $^1$H NMR: δ 11.98 (s, 1H), δ 4.74 (t, 2H), δ 4.25 (t, 2H), δ 3.42 (s, 2H), δ 2.26 (s, 6H), δ 1.74 (t, 2H), δ 1.25 (t, 6H); IR: 2976, 2937, 1732, 1712, 1645 cm$^{-1}$.

Example 8

The eighth example formula is set forth below for 4-hydroxy-2-methylbutan-2-yl 3-oxobutanoate:

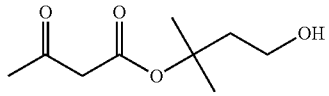

There are various methods to synthesis 4-hydroxy-2-methylbutan-2-yl 3-oxobutanoate. An explanation of how the formula was derived is described as follows. First, 3-methyl-1,3-butanediol (5.04 g, 48.44 mmol), Imidazole (3.60 g, 52.83 mmol), tert-Butyldimethylsilyl chloride (7.96 g, 52.81 mmol) and dichloromethane (70 mL) should be added together. The mixture can be capped and stirred vigorously in an ice bath for 5 hours. While the preferred method calls for heating the reaction to 100° C., it should be understood that higher temperatures may be utilized without departing from the nature of the invention. Then the resulting mixture can be run through filter paper to remove the white precipitate. The filtrate can be washed once with saturated NH$_4$Cl solution (25 mL) and the organic layer dried with MgSO$_4$, filtered, and evaporated down on a rotary evaporator. The resulting yellow liquid should be run through a 0.45 μm filter. To a 25 mL RBF was added the primary protected isopentyldiol (0.50 g, 2.27 mmol), 2,2,6-trimethyl-4H-1,3-dioxin-4-one (0.97 g, 6.82 mmol) and toluene (3 mL). The RBF was placed into a 140° C. sand bath with a reflux column and stirred vigorously for 45 minutes. To a 5 ml vial was added (0.10 g, 0.45 mmol), tetrabutylammonium fluoride hydrate (0.25 g, 0.80 mmol) and 2 mL THF. The vial was capped and stirred vigorously for 13 hours. Purification was performed with preparative TLC and analyzed by GCMS. MS m/e 173 [M-CH3].

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

While specific combinations of compounds are disclosed in specific embodiments, it should be understood that there exist numerous combinations of the different compound which may be utilized in the compound of the formulas for the present invention.

The foregoing disclosure and description of the invention are illustrative and explanatory thereof, and various changes in the compounds of illustrated formulas may be changed without departing from the spirit of the invention.

It is understood that the invention is not limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A compound having the formula:

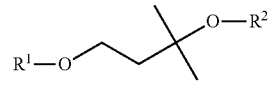

wherein either $R^1$ or $R^2$ is hydrogen, and $R^1$ or $R^2$ cannot be hydrogen at the same time;

when $R^2$ is hydrogen, $R^1$ is a structural composition selected from the group consisting of:

Acetoacetyl (CH$_3$COCH$_2$CO—), β-Hydroxybutyryl (CH$_3$CH(OH)CH$_2$CO—), (R)-β-Hydroxybutyryl or (S)-β-Hydroxybutyryl; and when $R^1$ is hydrogen, $R^2$ is a structural composition selected from a group consisting of: Acetoacetyl (CH$_3$COCH$_2$CO—), β-Hydroxybutyryl (CH$_3$CH(OH)CH$_2$CO—), (R)-β-Hydroxybutyryl (CH$_3$CH(OH)CH$_2$CO—) or (S)-β-Hydroxybutyryl (CH$_3$CH(OH)CH$_2$CO—); and any salt, ester, or polymer thereof.

2. The compound of claim 1 wherein $R^1$ is Acetoacetyl (CH$_3$COCH$_2$CO—) and $R^2$ is hydrogen.

3. The compound of claim 1 wherein $R^1$ is β-Hydroxybutyryl (CH$_3$CH(OH)CH$_2$CO—) and $R^2$ is hydrogen.

4. The compound of claim 1 wherein $R^1$ is (R)-β-Hydroxybutyryl and $R^2$ is hydrogen.

5. The compound of claim 1 wherein $R^1$ is (S)-β-Hydroxybutyryl and $R^2$ is hydrogen.

6. A compound having the formula:

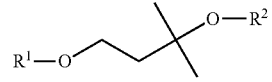

wherein either $R^1$ or $R^2$ is hydrogen, and $R^1$ or $R^2$ cannot be hydrogen at the same time;

when $R^2$ is hydrogen, $R^1$ is a structural composition selected from the group consisting of:

Acetoacetyl (CH$_3$COCH$_2$CO—), β-Hydroxybutyryl (CH$_3$CH(OH)CH$_2$CO—), (R)-β-Hydroxybutyryl or (S)-β-Hydroxybutyryl; and when $R^1$ is hydrogen, $R^2$ is a structural composition selected from a group consisting of: Acetoacetyl (CH$_3$COCH$_2$CO—), β-Hydroxybutyryl (CH$_3$CH(OH)CH$_2$CO—), (R)-β-Hydroxybutyryl (CH$_3$CH(OH)CH$_2$CO—) or (S)-β-Hydroxybutyryl (CH$_3$CH(OH)CH$_2$CO—).

7. The compound of claim 6 wherein $R^1$ is Acetoacetyl (CH$_3$COCH$_2$CO—) and $R^2$ is hydrogen.

8. The compound of claim 6 wherein $R^1$ is β-Hydroxybutyryl ($CH_3CH(OH)CH_2CO-$) and $R^2$ is hydrogen.

9. The compound of claim 6 wherein $R^1$ is (R)-β-Hydroxybutyryl and $R^2$ is hydrogen.

10. The compound of claim 6 wherein $R^1$ is (S)-β-Hydroxybutyryl and $R^2$ is hydrogen.

11. The compound of claim 6 wherein $R^2$ is Acetoacetyl ($CH_3COCH_2CO-$) and $R^1$ is hydrogen.

12. The compound of claim 6 wherein $R^2$ is β-Hydroxybutyryl ($CH_3CH(OH)CH_2CO-$) and $R^1$ is hydrogen.

13. The compound of claim 6 wherein $R^2$ is (R)-β-Hydroxybutyryl and $R^1$ is hydrogen.

14. The compound of claim 6 wherein $R^2$ is (S)-β-Hydroxybutyryl and $R^1$ is hydrogen.

15. A compound having the formula:

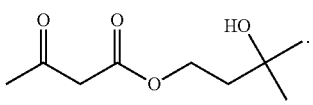

16. A compound having the formula:

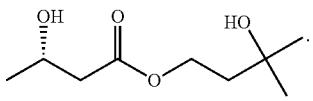

17. A compound having the formula:

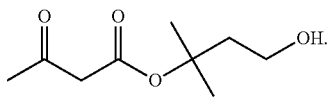

18. A compound having the formula:

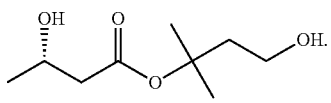

19. A compound having the formula:

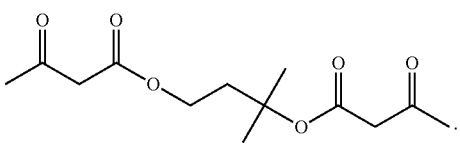 [SMILES: CC(=O)CC(=O)OCCC(C)(C)OC(=O)CC(C)=O]

20. A compound having the formula:

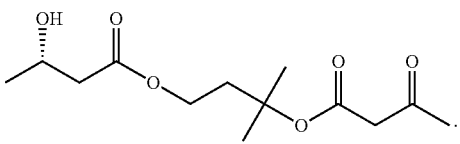 [SMILES: CC(=O)CC(=O)OC(C)(C)CCOC(=O)C[C@H](C)O]

* * * * *